(12) United States Patent
Ullrich et al.

(10) Patent No.: US 6,271,415 B1
(45) Date of Patent: Aug. 7, 2001

(54) S-(4-BIPHENYL)-THIOSULPHURIC ACIDS AND THEIR SALTS, METHOD FOR PRODUCING THE SAME AND METHOD FOR PRODUCING 4-MERCAPTOBIPHENYLS

(75) Inventors: Friedrich-Wilhelm Ullrich, Bergisch Gladbach; Helmut Fiege, Leverkusen; Wolfgang Eymann, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/529,917

(22) PCT Filed: Oct. 12, 1998

(86) PCT No.: PCT/EP98/06453

§ 371 Date: Apr. 19, 2000

§ 102(e) Date: Apr. 19, 2000

(87) PCT Pub. No.: WO99/20604

PCT Pub. Date: Apr. 29, 1999

(30) Foreign Application Priority Data

Oct. 22, 1997 (DE) .............................. 197 46 540

(51) Int. Cl.$^7$ ...................... C07C 381/00; C07C 381/04
(52) U.S. Cl. ................... 562/36; 562/30; 562/42
(58) Field of Search .................... 562/30, 41, 36, 562/42

(56) References Cited

U.S. PATENT DOCUMENTS

| | | | |
|---|---|---|---|
| 3,853,873 | 12/1974 | Elslager et al. | 260/256.5 R |
| 3,912,757 | 10/1975 | Mooradian | 260/330.5 |
| 5,659,088 | 8/1997 | Fiege et al. | 568/65 |
| 5,670,504 | 9/1997 | Bochis et al. | 514/247 |
| 6,117,970 | * 9/2000 | Popov et al. | 528/223 |

FOREIGN PATENT DOCUMENTS

| | | |
|---|---|---|
| 1253425 | 11/1971 | (GB) . |
| 2068952 | 8/1980 | (GB) . |
| 6-199871 | 9/1985 | (JP) . |

OTHER PUBLICATIONS

Angew. Chem, 79, 1967, (Month Unavailable), pp. 520–529, Distler, "Zur Chemie der Buntesalze".

J.A.C.S., vol. 66, (month unavailable) 1944, pp. 1674–1675, Lester et al, The Addition of 4–Mercaptobiphenyl to a Series of 1–Olefins.

Chem. Ber. 13, (month unavailable) 1980, pp. 385–390, W. Weber et al, Alkylierung cyclischer α,β–ungesättigter Ketone an der Doppelbindung.

J. Het. Chem. 15, Mar. 1978, pp. 281–284, L.H. Klemm et al, The Insertion and Extrusion of Heterosulfur Bridges. VI. Comparative Desulfurizations of Dibenzothiophene and Biphenylthiols (1).

Annales Univ. Mariae Curie–Sklodowska, Section AA, vol. 21, (month unavailable) 1966, Marian Janczewski et al, O syntezie kwasów orto—1 para–bifenylilotioglikolowych i ich niektórych pochodnych, pp. 65–83.

Tetrahedron Letters, vol. 21, (month unavailable) 1980, pp. 3099–3100, Testaferri et al, A Convenient Synthesis of Aromatic Thiols From Unactivated Aryl Halides.

Synthesis 9, Sep. 1983, pp. 751–755, Testaferri et al, Simple Syntheses of Aryl Alky Thioethers and of Aromatic Thiols from Unactivated Aryl Halides and Efficient Methods for Selective Dealkylation of Aryl Alkyl Ethers and Thioethers.

Tetrahedron Lett., No. 13, (month unavailable) 1966, pp. 1283–1286, Oae et al, The Reaction Of Elemental Sulfur with Organic Compounds. III. $^{1)}$ A New Type of Aromatic Displacement Reaction by Elemental Sulfur; Reaction with Halo Aromatics.

Chem. Ber. 99, (month unavailable) 1966, pp. 375–376, Adolf W. Wagner, Notiz über eine Vereinfachte Methode zur Datstellung von Thiophenolen.

Angew. Chem. 79, (month unavailable) 1967, pp. 525–528, Reaktionen der Buntesalze.

J. Org. Chem., vol. 24, (month unavailable) 1959, pp. 1598–1600, Hotelling et al, Synthesis of Mercaptophenols and alkyl Derivatives.

Beilstein reg No. 3405276 abs of Helv Chim Acta by Alcalay 30 pp. 578–583, 1947.*

* cited by examiner

*Primary Examiner*—Jean F. Vollano
(74) *Attorney, Agent, or Firm*—Joseph C. Gil; Diderico van Eyl

(57) ABSTRACT

The invention relates to novel S-(4-biphenyl)-thiosulfuric acids and their salts, to a method for producing them from S-(4-biphenyl)-thiosulfinic acids and their salts, and to a method for producing 4-mercaptobiphenyls from the S-(4-biphenyl)-thiosulfuric acids and their salts.

10 Claims, No Drawings

S-(4-BIPHENYL)-THIOSULPHURIC ACIDS AND THEIR SALTS, METHOD FOR PRODUCING THE SAME AND METHOD FOR PRODUCING 4-MERCAPTOBIPHENYLS

This application is the national phase and PCT/EP98/06453 filed Oct. 12, 1998 now WO99/20604.

BACKGROUND OF THE INVENTION

The present invention relates to novel S-(4-biphenyl)-thiosulphuric acids and salts thereof, to a process for their preparation starting from S-(4-biphenyl)-sulphinic acids and salts thereof and the preparation of 4-mercaptobiphenyls from the S-(4-biphenyl)-thiosulphuric acids and their salts.

4-Mercaptobiphenyls are important intermediates for preparing pharmaceutically and agiochemilcally active compounds (see, for example, BE-A 887 423, U.S. Pat. No. 3,912,757 and WO 96/25 936). Some processes for preparing 4-mercaptobiphenyls are already known; however, all of them are unsatisfactory.

Thus, biphenylsulphonyl chloride can be reduced using amalgamated zinc, metallic tin or tin(II) chloride (see, for example, J.A.C.S. 66, 1674 (1944), Chem. Ber. 13, 386 (1880) and Ann. Univ. Marie Curie-Sklodowska, Section Aa, Volume Date 1966 No. 21, 65 to 83 (1967)). In all of these processes, waste waters containing heavy metal salts are produced, the disposal of which involves great costs.

It is also possible to diazotize 4-aminodiphenyl, followed by reaction with potassium ethyl xanthate and hydrolysis of the resulting thioester (see DE-A 23 17 142, pp. 34 to 35). Here, water-soluble nickel chloride has to be employed which likewise passes into the waste water, where the disposal involves high costs.

The reaction of p-hydroxybiphenyl with dimethylthiocarbamoyl chloride followed by Newman-Kwart rearrangement and finally hydrolysis (see J. Het. Chem. 15, 281 (1978) and WO 96/25 936) affords 4-mercaptobiphenyl only in a yield of 39%.

When 4-bromobiphenyl is reacted with sodium methyl sulphide or sodium ethyl sulphide and the resulting thioether is cleaved, good yields of 4-mercaptobiphenyl (for example 96% of theory) are only obtained when handling of the carcinogenic hexamethylphosphoric triamide is accepted (see Tetrahedron Lett. 21, 3099 (1980)). The use of other solvents, for example dimethylformamide, results in considerably lower yields of 4-mercaptobiphenyl (for example 67% of theory—see Synthesis 9, 751 (1983)).

The reaction of 4-bromobiphenyl with elemental sulphur and the cleavage of the reaction product with lithium aluminium hydride to give 4-mercaptobiphenyl requires the use of lithium aluminium hydride, which is difficult to handle (see Tetrahedron Lett. 13, 1283 (1972).

Also known are reduction processes for preparing 4-mercaptobiphenyl starting from aromatic sulphonyl chlorides and aromatic disulphides. However, reduction with hydrogen and noble metal catalysts requires temperatures of up to 150° C. and pressures of up to 150 bar (see EP-A 2755), and reduction with red phosphorus and iodine necessarily leads to phosphoric acid and hydrogen chloride being produced (see Chem. Ber. 99, 375 (1966)) and requires red phosphorus, which is difficult to handle.

Finally, it is known that Bunte salts, i.e. salts of the type R-S-SO3M (R=organic radical, M=monovalent metal) in aqueous-acidic media generally hydrolyse to give thiols (see Angew. Chem. 79, 525 (1967)). However, in the present case disulphides were produced.

DESCRIPTION OF THE INVENTION

We have now found S-(4-biphenyl)-thiosulfuric acids and salts thereof corresponding to the formula (I)

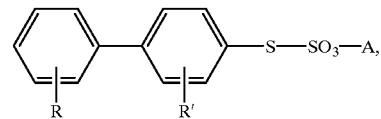

in which
A represents hydrogen, an equivalent of a metal atom or optionally substituted ammonium and
R and R' independently of one another each represent hydrogen, $C_1$–$C_6$-alkyl, $C_1$–$C_6$-alkoxy or halogen.

In the formula (I),
A preferably represents hydrogen, sodium, potassium, ½ calcium, ½ magnesium, ½ zinc, $NH_4$ or $NH_4$ substituted by 1 to 4 $C_1$–$C_6$-alkyl radicals and
R and R' independently of one another each represent hydrogen, methyl, ethyl, methoxy, ethoxy, fluorine or chlorine.

Particularly preferably, in the formula (I)
A represents hydrogen or sodium and
R and R' represent hydrogen.

Furthermore, we have found a process for preparing S-(4-biphenyl)-thiosulfuric acids and salts thereof of the formula (I) which is characterized in that S-(4-biphenyl)-sulfinic acids or salts thereof of the formula

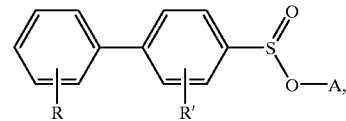

in which
A, R and R' are as defined in formula (I),
are reacted with an aqueous bisulfite solution at a pH in the range from 2 to 7.

The preferred and particularly preferred meanings of A, R and R' are also stated in formula (II) as in formula (I).

Some of the S-(4-biphenyl)-sulfinic acids and salts thereof of the formula (II) required as starting materials are known and can be prepared in a known manner or analogously thereto (see Ann. Univ. Marie Curie-Sklodowska, Section Aa, Volume Date 1966, No. 21, 49 to 64 (1967). The compound of the formula (II) in question does not have to be employed in pure form. It may, if appropriate, contain, for example, up to 25% by weight of the corresponding biphenylsulfonic acid and/or salts thereof. The compound of the formula (II) in question is preferably employed in the form of its sodium salt.

Very particular preference is given to using the sodium salt of S-(4-biphenyl)-sulfinic acid. Suitable aqueous bisulfite solutions are, in particular, aqueous alkali metal bisulphite solutions as are obtained, for example, when sulfur dioxide or sulfurous acid is introduced in an aqueous sodium hydroxide solution or an aqueous sodium carbonate solution or when sodium disulfite ($Na_2S_2O_5$) is dissolved in water. In addition to hydrogen sulfite ions, the aqueous bisulfite Solution may additionally contain, for example, sulphite ions, sulfurous acid or dissolved sulfur dioxide. The aqueous bisulfite solution may, for example, be 10 to 50% by weight strength, and it is preferably 25 to 45% by weight strength. Based on 1 mol of the compound of the formula (II) employed, it is possible to use, for example, an amount of aqueous bisulfite solution which corresponds to 1 to 5 mols of bisulfite. This amount is preferably from 1.5 to 3 mols.

If, after S-(4-biphenyl)-sulfinic acid or sulfinate of the formula (II) and aqueous bisulfite solution have been combined, the reaction mixture has a pH outside the range of 2 to 7, it is necessary to bring the pH into the range from 2 to 7, in the simplest case by addition of aqueous hydrochloric acid.

The reaction with the aqueous bisulfite solution is preferably carried out at a pH of from 3 to 5 which can, if appropriate, be established by addition of acid, for example by addition of aqueous hydrochloric acid. The more acidic the reaction and the longer the treatment in the more acidic medium, the higher the risk that the reaction will not stop at the stage of the S-(4-biphenyl)-thiosulfuric acids and salts thereof of the formula (II) but proceed to the formation of the corresponding bisdiphenyl disulfides of the formula (IV) (see further below). This may be desired (see further below).

If appropriate, water, for example in an amount of up to 5, preferably up to 3, parts by weight, based on one part by weight of the compound of the formula (II) used, may be added to the reaction with the aqueous bisulfite solution.

The reaction with the aqueous bisulfite solution can be carried out, for example, at temperatures in the range from 50 to 200° C. Preference is given to 120 to 170° C. If the reaction is to be carried out at temperatures above the boiling point (at atmospheric pressure) of the reaction mixture, the use of closed and pressure-tight reactors is required. In such cases, pressures of up to 12 bar, for example, may occur.

After the reaction has ended, the resulting salt of the S-(4-biphenyl)-thiosulfuric acid can be separated off, for example, in crude form by cooling the reaction mixture, for example to room temperature, and filtering off and, if appropriate, drying the precipitate which is then present. If desired, the product can be purified further, for example by extraction with boiling ethanol.

From the resulting salt of a S-(4-biphenyl)-thiosulfuric acid, generally the sodium salt, the corresponding S-(4-biphenyl)-thiosulfuric acid can be liberated by methods known per se. Preferably, the corresponding thiosulfuric acid is liberated from the salt of such a thiosulfuric acid by reaction on an acidic ion exchanger.

From free S-(4-biphenyl)-thiosulfuric acids, any salts of the respective S-(4-biphenyl)-thiosulfuric acid can be prepared by neutralization with an appropriate base.

We have also found a process for preparing 4-mercaptobiphenyls of the formula (III)

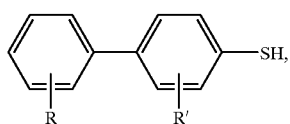

(III)

in which
R and R' are as defined in formula (I),
which is characterized in that S-(4-biphenyl)-thiosulfuric acids or salts thereof corresponding to the formula (I) are heated in the presence of a strong aqueous acid and the resulting bisdiphenyl disulfide of the formula

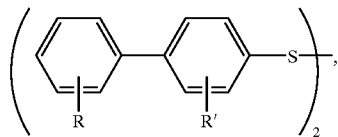

(IV)

in which
R and R' are as defined in formula (I), is reduced.

Suitable strong aqueous acids are, for example, sulphuric acid having concentrations of, for example, 0.05 to 30, preferably 1 to 30, % by weight. The amount of acid can be chosen such that, for example, a pH resulting in the reaction mixture is in the range from 0 to 2. The temperatures for the treatment with the strong aqueous acid can, for example, be in the range from 50 to 200° C., preferably in the range from 80 to 170° C.

From the reaction mixture, the bisdiphenyl disulfide prepared can be isolated by cooling the reaction mixture, for example to room temperature, and filtering off and, if appropriate, drying the precipitate which is then present.

The reduction of the bisdiphenyl disulfide of the formula (IV) in question to the corresponding 4-mercaptobiphenyl of the formula (III) can, for example, be carried out according to known methods, such as by reduction with sodium borohydride (see DE-A 44 20 777) by catalytic reduction with molybdenum sulfide catalysts at high pressures (see J. Org. Chem. 24, 1598 (1959) of by catalytic reduction with palladium catalysts, Raney cobalt or Raney nickel at high pressures in a liquid two-phase system (see DE-A 17 68 421 and JP-A (Japanese Published Specification) 60 199 871).

However, this reduction is preferably carried out as a catalytic reduction with metal catalysts of the 8th transition group of the PTE or with catalysts of the Raney type in alcoholic solution and in the presence of alkaline compounds, for example at temperatures in the range from 20 to 200° C. and pressures of up to 50 bar. Such reductions form part of the subject-matter of another patent application which was submitted simultaneously by the same applicant.

In the preparation according to the invention of 4-mercaptobiphenyls of the formula (III) from diphenyl sulfinic acids and salts thereof of the formula (11), it is not necessary to isolate the S-(4-biphenyl)-thiosulfuric acids and salts thereof of the formula (I) formed. It is possible, in the reaction with aqueous bisulfite solution for the formation of bisdiphenyl disulfides of the formula (IV), to establish suitable pHs during or after the reaction and/or to use sufficiently long reaction times, and thus to proceed directly to the corresponding bisdiphenyl disulfide of the formula (IV), without isolation of the S-(4-biphenyl)-thiosulfuric acids or salts thereof of the formula (I).

The bisdiphenyl disulfide of the formula (IV) in question does not have to be used in pure form for the reduction, in particular when it is to be carried out in the preferred manner described above. It is possible, for example, to mix the still moist filter cake obtained in the preparation with alcohol, an alkaline compound and catalyst and then to carry out the hydrogenation.

The S-(4-biphenyl)-sulfinic acids and salts thereof of the formula (II) which are required for the preparation according to the invention of 4-mercaptobiphenyls of the formula (III) can also be prepared in situ by reacting a corresponding diphenyl-4-sulfonyl chloride of the formula

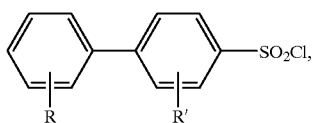

(V)

in which

R and R' are as defined in formula (I), at a pH in the range from 6 to 10 with aqueous bisulfite solution at from 40 to 80° C, followed by addition of $SO_2$ and heating to from 70 to 180° C. The bisdiphenyl disulfides of the formula (IV) are obtained directly, without intermediate isolation of the respective S-(4-biphenyl)-sulfinic acids or salts thereof of the formula (II) and without isolation of the respective S-(4-biphenyl)-thiosulfuric acids or salts thereof of the formula (I).

In this procedure, the pH during the reaction with aqueous bisulfite solution is preferably at from 7.5 to 9, and the temperature after the introduction of $SO_2$ is preferably at from 90 to 160° C. If the reaction is carried out above the boiling point of the reaction mixture (at atmospheric pressure), closed and pressure-tight reaction vessels have to be used.

The present invention provides a process for preparing 4-mercaptobiphenyls of the formula (III) via the corresponding novel S-(4-biphenyl)-thiosulfuric acids or salts thereof of the formula (I) which has a number of advantages. Thus, no waste water containing heavy metals is produced, the 4-mercaptobiphenyls of the formula (III) are obtained in high yields, no particular precautions for handling carcinogenic solvents and no reagents which are difficult to handle are required, no coproducts are produced and it is possible to avoid high pressures. The sum of these positive effects is particularly surprising since Angew. Chem. 79, 525 (1967) describes the acidic hydrolysis of Bunte salts as a generally suitable method for producing thiols. This is not so in the present case. Under the conditions described, the bisdiphenyl disulphides were formed here. These have to be cleaved reductively to give mercaptan. It is particularly surprising that, in spite of the many steps, biphenylsulfonyl chlorides can be converted by this route via S-(4-biphenyl)-thiosulfuric acids in high yields into 4-mercaptobiphenyl.

The invention is further described in the following illustrative examples in which all parts and percentages are by weight unless otherwise indicated.

EXAMPLE

Example 1

Preparation of a compound of the formula (I) from a compound of the formula (II)

140 g of diphenylsulfinic acid sodium salt (content 66.8% by weight, in addition to 10.5% by weight of diphenylsulfonic acid sodium salt) were stirred into 200 ml of water with 210 ml of aqueous bisulfite solution (39% by weight strength). Using 37% by weight strength aqueous hydrochloric acid, the pH was adjusted to 4. This mixture was heated in an autoclave to 150° C. and then stirred at 150° C. and a pressure between 4.1 and 4.3 bar for 2 hours. After cooling to room temperature, the resulting suspension was filtered off with suction and the isolated solid was dried. This gave 126.4 g of crude S-(4-biphenyl)-thiosulfuric acid as sodium salt in a yield of 78% of theory. In addition to biphenylsulfonic acid which had been entrained, unreacted sulfinic acid, but no bis-diphenyl disulfide, was detected as by-product by HPLC. The isolated solid was extracted with boiling ethanol. On cooling of the extract, S-(4-biphenyl)-thiosulphuric acid sodium salt precipitated out as monohydrate. The isolated product had the IR absorption bands characteristic of Bunte salts. Elemental analysis gave the following results (calc./found): C 47.1/47.4; If 3.6/3.6; 0 20.9/20.0; S 20.9/20.9; Na 7.5/8.0.

Example 2

Preparation of a compound of the formula (IV) from a compound of the formula (I)

100 ml of 10% by weight strength aqueous sulfuric acid were initially charged and heated to 100° C., and 17 g of the crude substance from Example 1 were then added. After a short period of time, at a pH of 0, a white solid precipitated out from the solution which initially was only slightly turbid. After 30 minutes of stirring at 100° C., the batch was cooled to room temperature and then filtered off with suction. The isolated solid was dried at 50° C. 200 mbar, giving 8.2 g of bisdiphenyl disulfide with a content of 86.3% by weight (HPLC). S-(4-biphenyl)-thiosulfuric acid was no longer detectable.

Example 3

Preparation of a compound of the formula (IV) from a compound of the formula (V)

440 ml of aqueous bisulfite solution (39% by weight strength) and 550 ml of water were initially charged with 125 ml of aqueous sodium hydroxide solution (45% by weight strength) and admixed with 2.2 g of triethylbenzylammonium chloride. The mixture was heated to 60° C. In the course of one hour, 289.5 g of diphenyl-4-sulfonyl chloride (96% by weight strength) were introduced, and the pH was simultaneously maintained at 8 by metered addition of 45% by weight strength aqueous sodium hydroxide Solution. pH control was also carried out during the 3 hours of extra stirring time. In an enamel autoclave, the reaction mixture was then admixed with 80 ml of sulphur dioxide and heated at 130° C. for 3 hours. The batch was stirred at 130° C. and a pressure between 4.4 and 6.9 bar for 6 hours. During this time, the stage of the S-(4-biphenyl)-thiosulfuric acid was passed through. The mixture was subsequently cooled to room temperature and vented and the resulting suspension was filtered off with suction. The filter cake was dried, giving 237.4 g of bisdiphenyl disulfide with a content of 78.3% by weight. This corresponds to a yield of 91.2% of theory.

Example 4

Preparation of a compound of the formula (III) from a compound of the formula (IV)

314 g of bisdiphenyl disulfide (obtained according to Example 3) were, as a moist filter cake, suspended in 1 l of ethanol and admixed with 44 g of sodium hydroxide and 24.7 g of sodium borohydride. The resulting mixture was stirred at 70° C. for 6 hours and the suspension obtained was then filtered off with suction at 70° C. The filter residue was washed with 250 ml of ethanol. The filtrate and the washing liquid were combined and adjusted to pH 1 using 900 ml of 7% by weight strength aqueous hydrochloric acid. The precipitated product was filtered off with suction, washed with 500 ml of water and dried. This gave 174.2 g of a white powder with a melting point of 111 to 113° C. Its 4-mercaptobiphenyl content was 98.3% by weight (determined iodometrically). This corresponds to a yield of 83.6% of theory, based on the diphenyl-4-sulfonyl chloride employed.

Example 5

Preparation of a compound of the formula (III) from a compound of the formula (IV)

270 g of bisdiphenyl disulfide were prepared as in Example 3 and, as a moist filter cake, suspended in 800 ml of ethanol and admixed with 44 g of sodium hydroxide and 5.5 g of Raney nickel. In an autoclave, the mixture was heated to 80° C., and a hydrogen pressure of 10 bar was then applied. After 4 hours, the uptake of hydrogen had ended. The batch was cooled and vented. After filtration with suction at 60° C., the mother liquor was acidified with 840 ml of 5.4% by weight strength aqueous hydrochloric acid, and the product precipitated out. The product was filtered off with suction, washed with 250 nil of water and dried. This gave 178.8 g of a white powder with a melting point of 110 to 112° C. The content of 4-mercaptodiplienyl was 91.8% by weight (determined iodometrically). This corresponds to a yield of 80.1% of theory, based on the diphenyl-4-sulfonyl chloride employed.

Although the present invention has been described in detail with reference to certain preferred versions thereof, other variations are possible. Therefore, the spirit and scope of the appended claims should not be limited to the description of the versions contained therein.

What is claimed is:

1. S-(4-biphenyl)-thiosulfuric acids and salts thereof corresponding to the formula

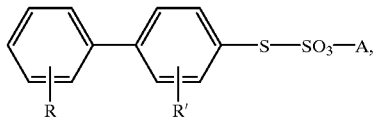

(I)

in which
- A represents hydrogen, an equivalent of a metal atom or optionally substituted ammonium and
- R and R' independently of one another each represent hydrogen, a $C_1$–$C_6$-alkyl group, a $C_1$–$C_6$-alkoxy group or a halogen.

2. Acids and salts of claim 1, wherein in formula (I)
- A represents hydrogen, sodium, potassium, ½ calcium, ½ magnesium, ½ zinc, $NH_4$ or $NH_4$ in which the hydrogen atoms are substituted with 1 to 4 $C_1$–$C_6$-alkyl radicals and
- R and R' independently of one another represent hydrogen, methyl, ethyl, methoxy, ethoxy, fluorine or chlorine.

3. A process for preparing S-(4-biphenyl)-thiosulfuric acids and corresponding to the formula (I)

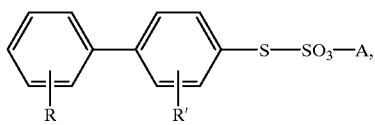

(I)

in which
- A represents hydrogen, an equivalent of a metal atom or optionally substituted ammonium and
- R and R' independently of one another each represent hydrogen, a $C_1$–$C_6$-alkyl group, a $C_1$–$C_6$-alkoxy group or a halogen, the process comprising reacting A) S-(4-biphenyl)-sulfinic acids or salts thereof of the formula (II)

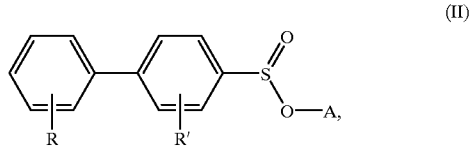

(II)

with
B) an aqueous bisulfite solution at a pH in the range from 2 to 7.

4. The process according to claim 3, wherein 1 to 5 mols of bisulfite are employed per mole of the compound of the formula (II) and the reaction with the aqueous bisulfite solution is carried out at temperatures in the range from 50 to 200° C.

5. A process for preparing 4-mercaptobiphenyls of the formula (III)

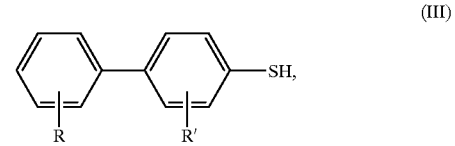

(III)

in which R and R' are independently of one another each represent hydrogen, a $C_1$–$C_6$-alkyl group, a $C_1$–$C_6$-alkoxy group or a halogen;

the comprising the steps of heating
A) S-(4-biphenyl)-thiosulfuric acids and salts corresponding to the formula (I)

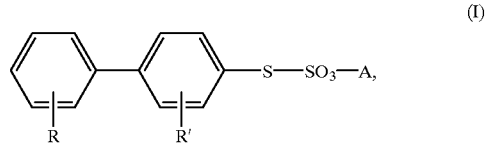

(I)

in which
- A represents hydrogen, an equivalent of a metal atom or optionally substituted ammonium and
- R and R' independently of one another each represent hydrogen, a $C_1$–$C_6$-alkyl group, a $C_1$–$C_6$-alkoxy group or a halogen, with
B) an aqueous bisulfite solution at a pH of from 2 to 7 in the presence of a strong aqueous acid and
C) reducing the resulting bisdiphenyl disulfide of the formula (IV)

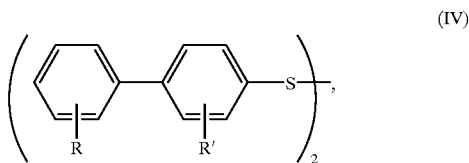

(IV)

wherein the compounds of formula (I) are prepared with a process that comprises the steps of (1) reacting S-(4-biphenyl)-sulfinic acids or salts thereof of the formula (II)

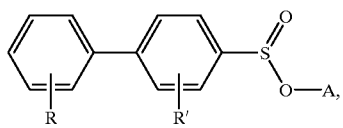

with (2) an aqueous bisulfite solution at a pH in the range from 2 to 7.

6. The process of claim 5, wherein the strong aqueous acid used is 0.05 to 30% by weight strength aqueous sulfuric acid and a pH in the range from 0 to 2 is maintained in the reaction mixtures.

7. The process of claim 5, wherein the heating in the presence of a strong aqueous acid is carried out to from 50 to 200° C.

8. The process of claim 5, wherein the reduction is carried out using sodium borohydride or as a catalytic reduction using molybdenum sulphide catalysts, palladium catalysts, Raney cobalt or Raney nickel.

9. The process of claim 5, wherein the S-(4-biphenyl)-thiosulfuric acids and the salts thereof of the formula (I) are not isolated.

10. The process of claim 5, wherein the S-(4-biphenyl)-sulfinic acids and salts thereof of the formula (II) required are prepared in situ by reacting a corresponding diphenyl-4-sulfonyl chloride of the formula (V)

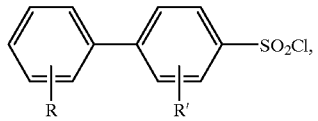

in which

R and R' are independently of one another represent hydrogen, methyl, ethyl, methoxy, ethoxy, fluorine or chlorine, at a pH in the range from 6 to 10 with aqueous bisulphite solution at from 40 to 80° C, followed by addition of $SO_2$ and heating to from 70 to 180° C.

* * * * *